(12) United States Patent
Ito et al.

(10) Patent No.: US 8,450,550 B2
(45) Date of Patent: *May 28, 2013

(54) PROCESS AND APPARATUS FOR PRODUCING PROPYLENE

(75) Inventors: Hirofumi Ito, Mito (JP); Jiro Yoshida, Yokohama (JP); Shuichi Funatsu, Yokohama (JP); Koji Ooyama, Yokohama (JP); Nobuyasu Chikamatsu, Yokohama (JP)

(73) Assignee: JGC Corporation, Tokyo (JP)

( * ) Notice: Subject to any disclaimer, the term of this patent is extended or adjusted under 35 U.S.C. 154(b) by 640 days.

This patent is subject to a terminal disclaimer.

(21) Appl. No.: 12/376,772

(22) PCT Filed: Sep. 19, 2007

(86) PCT No.: PCT/JP2007/068183
§ 371 (c)(1),
(2), (4) Date: Feb. 6, 2009

(87) PCT Pub. No.: WO2008/050558
PCT Pub. Date: May 2, 2008

(65) Prior Publication Data
US 2010/0179366 A1    Jul. 15, 2010

(30) Foreign Application Priority Data
Sep. 28, 2006  (JP) ................. 2006-264514

(51) Int. Cl.
*C07C 1/20* (2006.01)
*B01J 8/00* (2006.01)

(52) U.S. Cl.
USPC ........... 585/639; 585/259; 585/638; 585/640; 585/648; 585/651; 585/653; 422/134; 422/187; 502/77; 502/85; 502/213; 208/118; 208/120.1

(58) Field of Classification Search
USPC .... 585/259, 638–640, 648, 651, 653; 502/77, 502/85, 213; 422/134, 187, 189, 190, 194; 208/118, 120.01, 120.1
See application file for complete search history.

(56) References Cited

U.S. PATENT DOCUMENTS 4,083,888 A    4/1978  Caesar et al.
4,542,252 A    9/1985  Graziani et al.
(Continued)

FOREIGN PATENT DOCUMENTS

CN    1665911 A    9/2005
CN    1915937      2/2007
(Continued)

OTHER PUBLICATIONS

Martin, A. et al., Coupled conversion of methanol and C4 hydrocarbons to lower olefins (particularly, pp. 153-154).
(Continued)

*Primary Examiner* — Brian McCaig
(74) *Attorney, Agent, or Firm* — Leason Ellis LLP

(57) ABSTRACT

A process for producing propylene, which including feeding at least one of dimethyl ether and methanol to a reactor to be reacted in the presence of a catalyst; supplying an obtained reaction product to a separator by which low-boiling compounds having a boiling point of −50° C. or lower at atmospheric pressure among the reaction product are separated; and recycling a proportion of at least 70% of a total amount of the separated low-boiling compounds to said reactor.

6 Claims, 2 Drawing Sheets

U.S. PATENT DOCUMENTS

| | | | |
|---|---|---|---|
| 4,627,911 A | | 12/1986 | Chen et al. |
| 5,744,680 A | * | 4/1998 | Mulvaney et al. ............ 585/640 |
| 5,914,433 A | | 6/1999 | Marker |
| 5,990,369 A | | 11/1999 | Barger et al. |
| 6,646,175 B1 | | 11/2003 | Dath et al. |
| 2003/0139635 A1 | | 7/2003 | Hack et al. |
| 2003/0181777 A1 | | 9/2003 | Powers et al. |
| 2004/0122274 A1 | | 6/2004 | Van Egmond et al. |
| 2004/0192982 A1 | | 9/2004 | Kuechler et al. |
| 2007/0032379 A1 | | 2/2007 | Ito et al. |
| 2007/0265482 A1 | | 11/2007 | Tsunoda et al. |
| 2008/0189727 A1 | | 8/2008 | Tanaka |

FOREIGN PATENT DOCUMENTS

| | | |
|---|---|---|
| EP | 0485145 A1 | 5/1992 |
| GB | 2150593 | 7/1985 |
| JP | 60-120790 | 6/1985 |
| JP | 61-024526 | 2/1986 |
| JP | 62-070325 | 3/1987 |
| JP | 62-179592 | 8/1987 |
| JP | 04-273831 A | 9/1992 |
| JP | 2003535069 | 11/2003 |
| JP | 2005138000 | 6/2005 |
| JP | 2007-51143 | 3/2007 |
| WO | WO-02/10098 A1 | 2/2002 |
| WO | WO 2005/016856 | 2/2005 |
| WO | WO 2005/044760 A2 * | 5/2005 |
| WO | WO 2006/009099 | 1/2006 |
| WO | WO-2007/135045 A1 | 11/2007 |
| WO | WO-2007/135052 A1 | 11/2007 |

OTHER PUBLICATIONS

Nowak, S, et al., An improved method for producing low olefins and gasoline by coupled methanol/hydrocarbon cracking (CMHC), Proc. Int. Congr. Catal. 4, 1988, p. 1735-1742.

Office Action mailed Jun. 23, 2011 for the related U.S. Appl. No. 12/376,685.

European Search Report mailed Mar. 22, 2012 for the corresponding European Application No. 07806018.3.

Martin et al., Coupled Conversion of Methanol and $C_4$ Hydrocarbons to Lower Olefins, *Applied Catalysis*, 1989, pp. 149-155, vol. 50 No. 2.

Lucke et al., CMHC: coupled methanol hydrocarbon cracking Formation of lower olefins from methanol and hydrocarbons over modified zeolites, *Microporous and Mesoporous Materials*, 1999, pp. 145-157, vol. 29 No. 1-2.

Office Action of the corresponding Chinese Application No. 200780030388.8 mailed Mar. 12, 2012.

Office Action of the corresponding Japanese Application No. 2006-234007 mailed Apr. 17, 2012.

* cited by examiner

PROCESS AND APPARATUS FOR PRODUCING PROPYLENE

CROSS REFERENCE TO PRIOR APPLICATIONS

This is a U.S. National Phase application under 35 U.S.C. §371 of International Patent Application No. PCT/JP2007/068183, filed Sep. 19, 2007, and claims the benefit of Japanese Patent Application No. 2006-264514, filed Sep. 28, 2006 both of which are incorporated by reference herein. The International Application published on May 2, 2008 as WO 2008/050558 under PCT Article 21(2).

TECHNICAL FIELD

The present invention relates to a process for producing propylene by a dehydration-condensation reaction from dimethyl ether and/or methanol, and an apparatus for producing propylene.

Priority is claimed on Japanese Patent Application No. 2006-264514, filed on Sep. 28, 2006, the content of which is incorporated herein by reference.

BACKGROUND ART

Currently, there has been an increasing demand for a process for selective production of propylene because there is a difference in increases of demand for ethylene and propylene and there is an increase in the ethylene supply due to construction of ethane crackers in the Middle East. As a process for producing such propylene, a process is known whereby dimethyl ether (DME) or methanol is fed to a reactor equipped with a zeolite catalyst to obtain a reaction product containing propylene and the propylene is separated from the reaction product.

It is known that, when a reaction product containing propylene is obtained by the reactor mentioned above, a yield of lower olefins such as propylene, etc. can be increased since a ratio of propylene contained in the reaction product can be increased by lowering the partial pressure of dimethyl ether (DME) or methanol occupied in the reactor (Patent Literature 1).

A previously known method involves feeding steam or inert gas into a reactor in order to lower the partial pressure of dimethyl ether (DME) or methanol used as a raw material contained inside the reactor (Patent Literature 2). Particularly, steam is produced in a large amount when dimethyl ether (DME) or methanol is reacted to obtain a reaction product containing propylene, and thus the steam can be conveniently used as a means to lower the partial pressure of dimethyl ether (DME) or methanol contained inside the reactor in view of its convenient supply and low cost.

Patent Literature 1: U.S. Pat. No. 4,083,888
Patent Literature 2: JP-A-2003-535069

DISCLOSURE OF THE INVENTION

Problems that the Invention is to Solve

However, when a reaction product containing propylene is obtained using dimethyl ether (DME) or methanol as a raw material, if a large amount of steam is introduced in order to increase the yield of propylene by lowering the partial pressure of the raw material inside the reactor, aluminum, which is a framework component of a zeolite catalyst, is eliminated from the zeolite framework due to the presence of the steam. As a result, there has been a problem in that a non-regenerable deactivation (the permanent deactivation) of the catalyst occurs and thereby the deactivation of the catalyst in the reactor is accelerated.

In addition, in order to inhibit the deactivation of the catalyst in the reactor, there is a method wherein an inert gas is introduced into a reactor to lower the partial pressure of a raw material in the reactor, but there is a problem in that there is a need for additional supply of an inert gas such as helium, nitrogen and the like, thereby increasing the cost of the propylene production.

In view of the above-mentioned problems of the conventional technology, the invention has been completed, and it is an object of the invention to provide a process for producing propylene and an apparatus for producing propylene whereby propylene can be produced at a low cost by increasing the yield of propylene by inhibiting the catalyst deactivation.

Means for Solving the Problems

To achieve the above object, the invention provides a process for producing propylene as described below. That is, a process for producing propylene of the invention includes feeding at least one of dimethyl ether and methanol to a reactor to be reacted in the presence of a catalyst; supplying an obtained reaction product to a separator whereby low-boiling compounds having a boiling point of $-50°$ C. or lower at atmospheric pressure among the reaction product are separated; and recycling a proportion of at least 70% of a total amount of said separated low-boiling compounds to said reactor.

It is preferred that a proportion of at least 80% of a total amount of said separated low-boiling compounds be recycled to said reactor. And said low-boiling compounds are recycled to said reactor after at least some of the low-boiling compounds are converted to a $C_4$~$C_{10}$ hydrocarbon.

In addition, it is preferred that at least a part of $C_4$~$C_6$ hydrocarbons separated by said separator be recycled to said reactor. It is preferred that the catalyst be a MFI zeolite catalyst. It is preferred that the catalyst be an alkaline earth metal-containing MFI zeolite catalyst, wherein the alkaline earth metal-containing MFI zeolite has a Si/Al molar ratio of from 10 to 300 and an alkaline earth metal/Al molar ratio of from 0.75 to 15.

Further, the invention provides an apparatus for producing propylene as described hereafter. That is, the apparatus for producing propylene according to the invention includes:

a reactor wherein at least one of dimethyl ether and methanol is reacted in the presence of a catalyst to produce a reaction product containing propylene;

a separator whereby at least propylene, and low-boiling compounds having a boiling point of $-50°$ C. or lower at atmospheric pressure are separated from said reaction product obtained in said reactor; and an oligomerization reactor wherein at least some of said low-boiling compounds are converted to a $C_4$~$C_{10}$ hydrocarbon.

A percentage (%) used herein means "weight %".

Effects of the Invention

According to a process for producing propylene of the invention, when at least one of dimethyl ether and methanol as a raw material is fed to a reactor to obtain a reaction product containing propylene, a proportion of at least 70% of a total amount of said low-boiling compounds having a boiling point of $-50°$ C. or lower obtained by the separator is recycled to the reactor. Due to this, the partial pressure of the raw material inside the reactor is lowered so that the yield of propylene is increased, and thereby propylene can be efficiently produced.

In addition, said low-boiling compounds having a boiling point of −50° C. or lower obtained by the separator are recycled to the reactor for lowering the partial pressure of at least one of dimethyl ether and methanol as a raw material inside the reactor. As a result, there is no need for additional supply of an inert gas so that the yield of propylene can be increased at a low cost. Further, said low-boiling compounds having a boiling point of −50° C. or lower are wholly recycled to the reactor so that a process for separating them into methane, ethane, ethylene and the like, can be omitted, and thereby energy needed for the separation can be reduced.

Moreover, according to the invention, the low-boiling compounds having a boiling point of −50° C. or lower obtained by the separator are used for lowering the partial pressure of at least one of dimethyl ether and methanol as a raw material inside the reactor. Thereby, in comparison with the conventional methods in which the obtained steam is recycled to a reactor, it is difficult for aluminum to be eliminated from the framework of the zeolite catalyst in the reactor. Due to this, it becomes possible to reduce an amount of the charged catalyst and to extend the cycle of the catalyst regeneration, and thereby costs for the facility and operation can be cut down.

DESCRIPTION OF REFERENCE NUMERALS AND SIGNS

10: APPARATUS FOR PRODUCING PROPYLENE
11: REACTOR
12: SEPARATOR
13: OLIGOMERIZATION REACTOR

BEST MODE FOR CARRYING THE INVENTION

Hereafter, best modes for carrying out a process and an apparatus for producing propylene according to the invention will be described. However, the following embodiment is specifically explained only for easier understanding of the principle of the invention, and the invention is not to be limited thereto, unless otherwise described.

Figure 1:
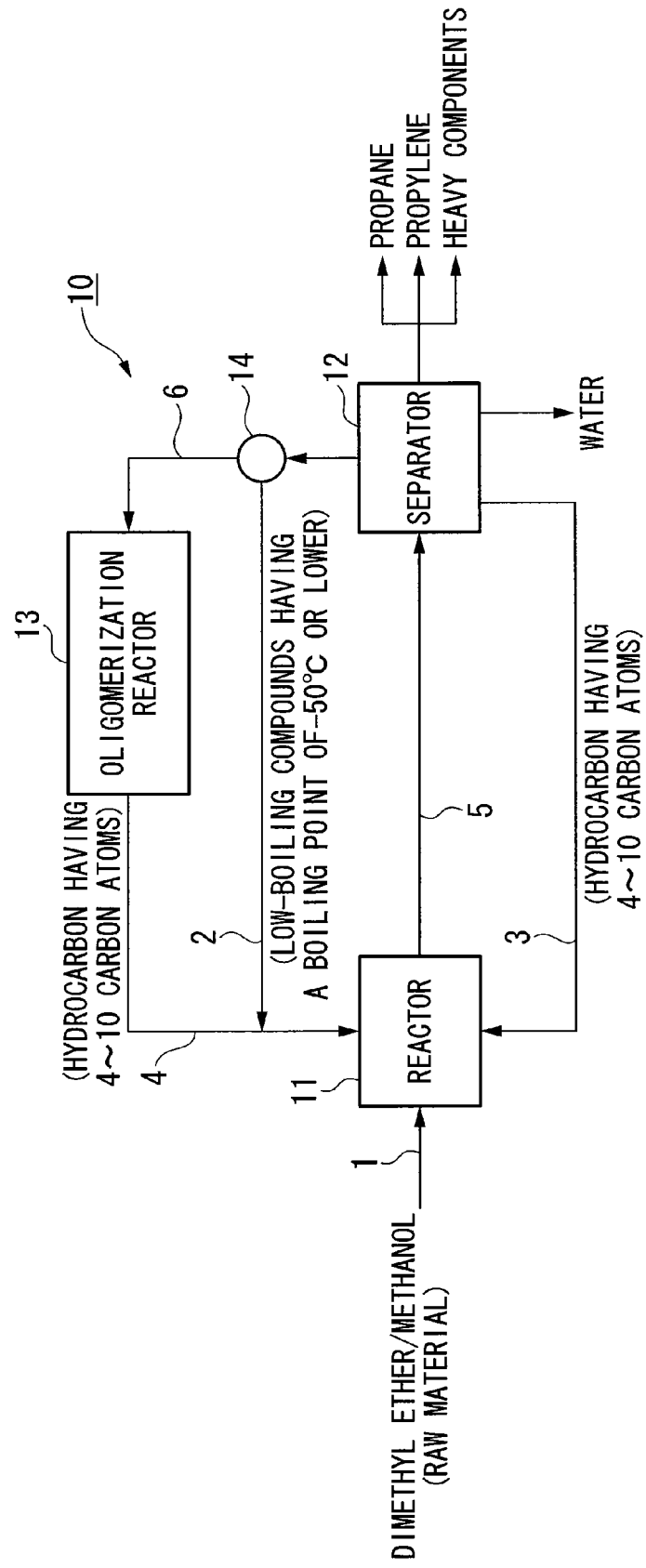
FIG. 1 is a flow diagram of an embodiment of an apparatus for producing propylene and a process for producing propylene by using the apparatus according to the invention.

FIG. 1 is a flow diagram to illustrate the gist of an apparatus for producing propylene and a process for producing propylene by using the apparatus according to the invention. An apparatus 10 for producing propylene in this embodiment is equipped with a reactor 11, a separator 12 and an oligomerization reactor 13. Dimethyl ether/methanol as a raw material, low-boiling compounds having a boiling point of −50° C. or lower and a $C_4$~$C_6$ hydrocarbon recycled from the separator 12 described below, and a $C_4$~$C_{10}$ hydrocarbon provided from the oligomerization reactor 13 are reacted in the reactor 11 charged with a catalyst, to produce a reaction product containing propylene.

In the separator 12, the reaction product containing propylene is separated and purified to obtain propylene, propane, heavy components, water, the low-boiling compounds having a boiling point of −50° C. or lower, the $C_4$~$C_{10}$ hydrocarbon and the like. Among these, the proportion of at least 70% of the total weight of the separated low-boiling compounds having a boiling point of −50° C. or lower is recycled to the reactor 11, and some of the remaining amount is supplied to the oligomerization reactor 13. In the oligomerization reactor 13, some of the low-boiling compounds having a boiling point of −50° C. or lower obtained by the separator 12 are oligomerized to produce $C_4$~$C_{10}$ hydrocarbons.

A process will be now described for producing propylene in the invention by using the apparatus for producing propylene including such constituents. First, at least one of dimethyl ether and methanol used as a raw material is fed to the reactor 11 through a pipe 1. In addition, at least one of dimethyl ether and methanol can include gas such as steam methane, ethane, nitrogen, argon, carbon dioxide and the like.

In addition, some of the low-boiling compounds having a boiling point of −50° C. or lower separated by the separator 12 are supplied to the reactor 11 through a pipe 2. Further, the $C_4$~$C_6$ hydrocarbon separated by the separator 12 is supplied to the reactor 11 through a pipe 3. Moreover, the $C_4$~$C_{10}$ hydrocarbon obtained in the oligomerization reactor 13 is supplied to the reactor 11 through a pipe 4.

A gas mixture supplied to the reactor 11, including dimethyl ether/methanol as a raw material, the low-boiling compounds having a boiling point of −50° C. or lower and the $C_4$~$C_6$ hydrocarbon recycled from the separator 12, and the $C_4$~$C_{10}$ hydrocarbon obtained from the oligomerization reactor 13, is reacted in the reactor 11 to obtain the reaction product containing propylene.

In this process which includes obtaining the reaction product containing propylene, the partial pressure of dimethyl ether/methanol as a raw material contained in the reactor is maintained at, for example, 0.005 MPa~0.20 MPa, by recycling the low-boiling compounds having a boiling point of −50° C. or lower separated by the separator 12 to the reactor 11.

A catalyst is charged in the reactor 11, and a reaction product including propylene, low-boiling compounds having a boiling point of −50° C. or lower, a $C_4$~$C_6$ hydrocarbon, propane, heavy components, water and the like can be obtained by a dehydration-condensation reaction, a catalytic cracking reaction and the like via the function of the catalyst.

As a catalyst in the reactor 11, a MFI zeolite catalyst, an alkaline earth metal-containing MFI zeolite catalyst, a silico-alumino-phosphate catalyst and the like are used, and a system such as a fluidized-bed reaction system, a fixed-bed reaction system, a moving-bed reaction system and the like is used. Among these, the MFI zeolite catalyst is preferred and the alkaline earth metal-containing MFI zeolite catalyst is more preferred because a lower hydrocarbon is obtained at a high yield.

As an example of the reaction conditions in the reactor 11, said gas mixture is contacted with the catalyst at a temperature of from 350° C. to 600° C. In addition, it is preferable that the weight hourly space velocity (denoted as "WHSV" hereafter), which corresponds to a mass of dimethyl ether (denoted as "DME" hereafter) fed per unit catalyst weight·per unit hour, be selected from the range of from 0.025 g—DME/g-catalyst·hour to 50 g—DME/g-catalyst·hour and that the pressure be selected from the range of from atmospheric pressure to 1 MPa.

If the gas mixture is contacted with the catalyst at a temperature of below 350° C., it is not economical since a production rate of the intended reaction product is low. Meanwhile, if the gas mixture is contacted with the catalyst at a temperature of above 600° C., the catalyst deactivation is rapid and thereby increases the production of by-products such as methane and the like.

In addition, if the WHSV is lower than 0.025 g—DME/g-catalyst·hour, it is not economical since the productivity per a unit volume of a fixed-bed reaction system becomes low. Meanwhile, if the WHSV is more than 50 g—DME/g-catalyst·hour, a lifetime or activity of the catalyst becomes insufficient.

The content ratio of an intended lower hydrocarbon in the reaction product can be varied by controlling the reaction conditions in the reactor 11. For example, in order to increase the proportion of propylene, it is preferable to maintain the reaction pressure at a low pressure.

The reaction product including propylene as a main component, obtained in the reactor 11, is supplied through a pipe 5 to a heat-exchanger, which is not shown in FIG. 1, to be cooled, and then supplied to the separator 12. In the separator 12, propylene or propane is recovered by separating the reaction product into each component, i.e., propylene, propane, low-boiling compounds having a boiling point of −50° C. or lower, a $C_4$~$C_6$ hydrocarbon, heavy components, water and the like.

Among each component separated by the separator 12, at least a part of a $C_4$~$C_6$ hydrocarbon is recycled to the reactor 11 through the pipe 3. Meanwhile, at least 70% of the obtained total amount of the low-boiling compounds having a boiling point of −50° C. or lower is recycled to the reactor 11 through the pipe 2. In addition, among the low-boiling compounds having a boiling point of −50° C. or lower, the remaining amount thereof excluding the amount recycled to the reactor 11 through the pipe 2 is supplied to the oligomerization reactor 13 through a pipe 6. As a result, the low-boiling compounds having a boiling point of −50° C. or lower separated from the reaction product are divided into a portion thereof recycled to the reactor 11 through the pipe 2, a portion thereof supplied to the oligomerization reactor 13 through the pipe 6, and the like. In such a division, for example, they are divided in a specified ratio by a divider 14 to allow for flowing in each direction.

The oligomerization reactor 13 produces a $C_4$~$C_{10}$ hydrocarbon by oligomerizing the low-boiling compounds having a boiling point of −50° C. or lower supplied through the pipe 6 from the divider 14. This $C_4$~$C_{10}$ hydrocarbon is supplied to the reactor 11 through the pipe 4.

According to the apparatus for producing propylene and the process for producing propylene in the invention as described above, when the reaction product including propylene is obtained from the reactor 11 in which at least one of dimethyl ether and methanol is fed, a proportion of at least 70% of the total amount of the low-boiling compounds having a boiling point of −50° C. or lower obtained by the separator 12 is recycled to the reactor 11. Due to this, the partial pressure of the raw material inside the reactor is lowered so that the yield of propylene is increased, and thereby propylene can be efficiently produced.

In addition, the low-boiling compounds having a boiling point of −50° C. or lower obtained by the separator 12 are recycled to the reactor 11 for lowering the partial pressure of at least one of dimethyl ether and methanol as a raw material inside the reactor 11. As a result, the partial pressure of the raw material can be lowered without additionally supplying an inert gas and the like, and thus the yield of propylene can be increased at a low cost.

Moreover, the low-boiling compounds having a boiling point of −50° C. or lower obtained by the separator 12 are used for lowering the partial pressure of at least one of dimethyl ether and methanol as a raw material inside the reactor 11. Thereby, in comparison with the conventional methods in which the obtained steam is recycled to the reactor, it is difficult for aluminum to be eliminated from the framework of the charged zeolite catalyst. Due to this, it becomes possible to reduce an amount of the charged catalyst and to extend the cycle of the catalyst regeneration, and costs of the facility and operation can be cut down.

Further, although the low-boiling compounds having a boiling point of −50° C. or lower obtained by the separator 12 include methane, ethane, ethylene and the like, these low-boiling compounds having a boiling point of −50° C. or lower including methane, ethane, ethylene and the like are wholly recycled into the reactor 11 to lower the partial pressure of the raw material. Accordingly, a process for separating the low-boiling compounds into each component such as methane, ethane, ethylene and the like can be omitted so that energy needed for the separation can be reduced, and thereby the production of propylene can be carried out at a much lower cost.

EXAMPLES

Hereafter, the invention will be more specifically described with reference to the following examples, and the invention is not limited thereto, unless otherwise described.

<Preparation of a Catalyst>

A calcium-containing MFI zeolite was prepared by the method of Japanese Unexamined Patent Application Publication No. 2005-138000. That is, a raw material solution which consists of 9.50 g of $Al(NO_3)_3.9H_2O$ and 10.92 g of $Ca(CH_3COO)_2.H_2O$ for the zeolite preparation was dissolved in 750 g of water. To the resultant solution, a solution in which 500 g of CATALOID SI-30 (produced by CATALYSTS and CHEMICALS ND. Co., Ltd.) water glass was dissolved in 333 g of water, 177.5 g of 6 mass % aqueous NaOH solution, 317.6 g of 21.3 mass % aqueous tetrapropyl ammonium bromide solution, and 15.0 g (which is equivalent to 10 mass % of the quantity of the zeolite catalyst which was synthesized without adding a seed crystal) of an ammonium type MFI zeolite (produced by Zeolyst International, having Si/Al atomic ratio of 70) having an average particle diameter of 0.5 μm as a zeolite seed crystal were added while stirring to obtain an aqueous gel mixture. Subsequently, this aqueous gel mixture was put into a 3-L autoclave, and agitated at 160° C. under self-pressure for 18 hours to perform hydrothermal synthesis. After filtering and washing the white solid product by hydrothermal synthesis, it was dried at 120° C. for 5 hours, and was calcined at 520° C. in air for 10 hours. That calcined product was impregnated with 0.6N hydrochloric acid, and the resultant mixture was stirred at room temperature for 24 hours, to exchange the type of zeolite to a proton type. Then, after being filtered and washed with water the resultant product was dried at 120° C. for 5 hours and calcined at 520° C. in air for 10 hours to obtain a proton type calcium-containing MFI zeolite (denoted as "HCaMFI" hereafter) catalyst.

<Production of a Lower Hydrocarbon>

A lower hydrocarbon was synthesized from dimethyl ether as a raw material using the above HCaMFI catalyst as a catalyst.

Example 1

Dimethyl ether flowing at a rate of 1200 Ncm³/hour, methane flowing at a rate of 600 Ncm³/hour and nitrogen flowing at a rate of 600 Ncm³/hour were mixed and fed to an isothermal reactor charged with the HCaMFI catalyst, thereby reacting them at 530° C. under atmospheric pressure. The weight hourly space velocity (WHSV), which is the ratio of the supplied quantity of dimethyl ether (DME) as a raw material to the quantity of the catalyst, was set to be 9.6 g-DME/(g-catalyst·hour). And the yield and conversion of each of a hydrocarbon having at most 2 carbon atoms, propylene, propane and a hydrocarbon having at least 4 carbon atoms, with respect to the total amount of the supplied dimethyl ether (DME) were measured.

Example 2

Dimethyl ether flowing at a rate of 1200 Ncm³/hour, ethylene flowing at a rate of 600 Ncm³/hour and nitrogen flowing at a rate of 600 Ncm³/hour were mixed and fed to an isothermal reactor charged with the HCaMFI catalyst, thereby reacting them at 530° C. under atmospheric pressure. The weight hourly space velocity (WHSV), which is the ratio of the supplied quantity of dimethyl ether (DME) as a raw material to the quantity of the catalyst, was set to be 9.6 g-DME/(g-catalyst·hour). And the yield and conversion of each of a hydrocarbon having at most 2 carbon atoms, propylene, propane, and a hydrocarbon having at least 4 carbon atoms, with respect to the total amount of the supplied dimethyl ether (DME) were measured.

Comparative Example 1

Dimethyl ether flowing at a rate of 1200 Ncm³/hour, steam flowing at a rate of 900 Ncm³/hour and nitrogen flowing at a rate of 300 Ncm³/hour were mixed and fed to an isothermal reactor charged with the HCaMFI catalyst, thereby reacting them at 530° C. under atmospheric pressure. The weight hourly space velocity (WHSV), which is the ratio of the supplied quantity of dimethyl ether (DME) as a raw material to the quantity of the catalyst, was set to be 9.6 g-DME/(g-catalyst·hour). And the yield and conversion of each of a hydrocarbon having at most 2 carbon atoms, propylene, propane, and a hydrocarbon having at least 4 carbon atoms, with respect to the total amount of the supplied dimethyl ether (DME) were measured.

Comparative Example 2

Dimethyl ether flowing at a rate of 1200 Ncm³/hour and nitrogen flowing at a rate of 1200 Ncm³/hour were mixed and fed to an isothermal reactor charged with the HCaMFI catalyst, thereby reacting them at 530° C. under atmospheric pressure. The weight hourly space velocity (WHSV), which is the ratio of the supplied quantity of dimethyl ether (DME) as a raw material to the quantity of the catalyst, was set to be 9.6 g-DME/(g-catalyst·hour). And the yield and conversion of each of a hydrocarbon having at most 2 carbon atoms, propylene, propane, and a hydrocarbon having at least 4 carbon atoms, with respect to the total amount of the supplied dimethyl ether (DME) were measured.

The results of the measurements in Examples 1 and 2 and Comparative Examples 1 and 2 are shown in Table 1.

TABLE 1

| | | Example 1 | Example 2 | Comparative Example 1 | Comparative Example 2 |
|---|---|---|---|---|---|
| Amount of the supplied raw material (Ncm³/h) | DME | 1200 | 1200 | 1200 | 1200 |
| | steam | 0 | 0 | 900 | 0 |
| | methane | 600 | 0 | 0 | 0 |
| | ethylene | 0 | 600 | 0 | 0 |
| | nitrogen | 600 | 600 | 300 | 1200 |
| Conversion of DME (%) | | 100 | 100 | 98 | 100 |
| Yield of hydrocarbon from DME (wt %) | $\leq C_2$ | 9 | 8 | 7 | 10 |
| | propylene | 40 | 40 | 39 | 40 |
| | propane | 1 | 1 | 1 | 1 |
| | $\geq C_4$ | 50 | 51 | 53 | 49 |

According to the results shown in Table 1, Examples 1 and 2 and Comparative Examples 1 and 2 had no difference in the yield of each of a hydrocarbon having at most 2 carbon atoms, propylene, propane, and a hydrocarbon having at least 4 carbon atoms, with respect to the total amount of the supplied dimethyl ether (DME); however, the conversion of Comparative Example 1 was decreased in comparison with Examples 1 and 2 without using steam.

From these results, it was confirmed that, in comparison with the case of using steam, the conversion of dimethyl ether (DME) increased by using the low-boiling compounds having a boiling point of −50° C. or lower such as methane and ethylene, etc. instead of steam to lower the partial pressure of dimethyl ether (DME) as a raw material in the reactor, and thereby propylene can be efficiently produced.

Example 3

A reaction product (83% conversion of methanol) from the dehydration reaction of methanol of 1628 NL/hour which is converted with respect to the supplied amount of dimethyl ether was fed to a simulated isothermal reactor charged with the HCaMFI catalyst, then reacting them at the temperature of 400° C. at the inlet of the catalyst bed under the inlet pressure of 0.2 MPa-G, and at the temperature of 550° C. at the outlet of the catalyst bed. An amount of 70% of the low-boiling compounds having a boiling point of −50° C. or lower separated from the reaction product effluent from the reactor was recycled to the reactor and then subjected to the reaction. In addition, a total amount of the $C_4$~$C_6$ hydrocarbon separated from the reaction product was also recycled to the reactor. The weight hourly space velocity (WHSV), which is the ratio of the supplied quantity of dimethyl ether (DME) as a raw material to the quantity of the catalyst, was set to be 4.8 g-DME/(g-catalyst·hour). When the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

Example 4

The reaction test was performed in the same way as in Example 3 except that 80% of the low-boiling compounds having a boiling point of −50° C. or lower separated from the reaction product produced in the reactor were recycled to the reactor. Then, when the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

Example 5

The reaction test was performed in the same way as in Example 3 except that 90% of the low-boiling compounds having a boiling point of −50° C. or lower separated from the reaction product produced in the reactor were recycled to the reactor. Then, when the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

Example 6

The reaction test was performed in the same way as in Example 3 except that 95% of the low-boiling compounds having a boiling point of −50° C. or lower separated from the reaction product produced in the reactor were recycled to the reactor. Then, when the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

Comparative Example 3

The reaction test was performed in the same way as in Example 3 except that 25% of the low-boiling compounds having a boiling point of −50° C. or lower separated from a reaction product produced in the reactor were recycled to the reactor. Then, when the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

Comparative Example 4

The reaction test was performed in the same way as in Example 3 except that 50% of the low-boiling compounds having a boiling point of −50° C. or lower which from a reaction product produced in the reactor were recycled to the reactor. Then, when the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

Comparative Example 5

The reaction test was performed in the same way as in Example 3 except that 60% of the low-boiling compounds having a boiling point of −50° C. or lower separated from a reaction product produced in the reactor were recycled to the reactor. Then, when the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

Comparative Example 6

The reaction test was performed in the same way as in Example 3 except that 65% of the low-boiling compounds having a boiling point of −50° C. or lower separated from a reaction product produced in the reactor were recycled to the reactor. Then, when the flow rate of the low-boiling compounds having a boiling point of −50° C. or lower was stabilized, the flow rates of the low-boiling compounds having a boiling point of −50° C. or lower and the $C_4$~$C_6$ hydrocarbon, the yield of each of a hydrocarbon having at most 2 carbon atoms, propylene, propane, and a hydrocarbon having at least 7 carbon atoms with respect to the total amount of the supplied dimethyl ether (DME), and the partial pressure of dimethyl ether (DME) were measured.

The results of the measurements in these Examples 3~6 and Comparative Examples 3~6 are shown in Table 2.

TABLE 2

| | | Comp. Example 3 | Comp. Example 4 | Comp. Example 5 | Comp. Example 6 | Example 3 | Example 4 | Example 5 | Example 6 |
|---|---|---|---|---|---|---|---|---|---|
| Partial pressure of DME (MPa) | | 0.114 | 0.109 | 0.106 | 0.104 | 0.101 | 0.095 | 0.084 | 0.069 |
| Amount of supplied raw material (NL/h) | DME | 1628 | 1628 | 1628 | 1628 | 1628 | 1628 | 1628 | 1628 |
| | $C_4$~$C_6$ (recycled) | 874 | 915 | 920 | 943 | 967 | 1013 | 1074 | 1109 |

TABLE 2-continued

|  |  | Comp. Example 3 | Comp. Example 4 | Comp. Example 5 | Comp. Example 6 | Example 3 | Example 4 | Example 5 | Example 6 |
|---|---|---|---|---|---|---|---|---|---|
| Recycled ratio of low-boiling compound having a boiling point of −50° C. or lower (%) | | 25 | 50 | 60 | 65 | 70 | 80 | 90 | 95 |
| Flow rate of low-boiling compound having a boiling point of −50° C. or lower (NL/h) | | 143 | 362 | 470 | 582 | 695 | 920 | 1582 | 2745 |
| Conversion of DME (%) | | 100 | 100 | 100 | 100 | 100 | 100 | 100 | 100 |
| Hydrocarbon yield from DME (%) | ≦$C_2$ | 25 | 20 | 18 | 17 | 16 | 13 | 10 | 8 |
| | Propylene | 50 | 58 | 63 | 64 | 65 | 67 | 70 | 71 |
| | Propane | 8 | 7 | 6 | 6 | 6 | 6 | 6 | 7 |
| | ≧$C_7$ | 17 | 15 | 13 | 13 | 13 | 14 | 14 | 14 |

According to the results from Comparative Examples 3~6 as shown in Table 2, it can be seen that, when the proportion of the low-boiling compounds having a boiling point of −50° C. or lower was lower than 70% recycled to the reactor, there was only a slight change in the amount of lowering of the partial pressure of dimethyl ether and that there was no contribution to enhancing the yield of propylene. Meanwhile, from the results of Examples 3~6 as shown in Table 2, it can be seen that, when the proportion of the low-boiling compounds having a boiling point of −50° C. or lower recycled to the reactor was at least 70%, particularly at least 80%, there was a large change in the amount of lowering of the partial pressure of dimethyl ether, thereby enhancing the yield of propylene.

Figure 2:
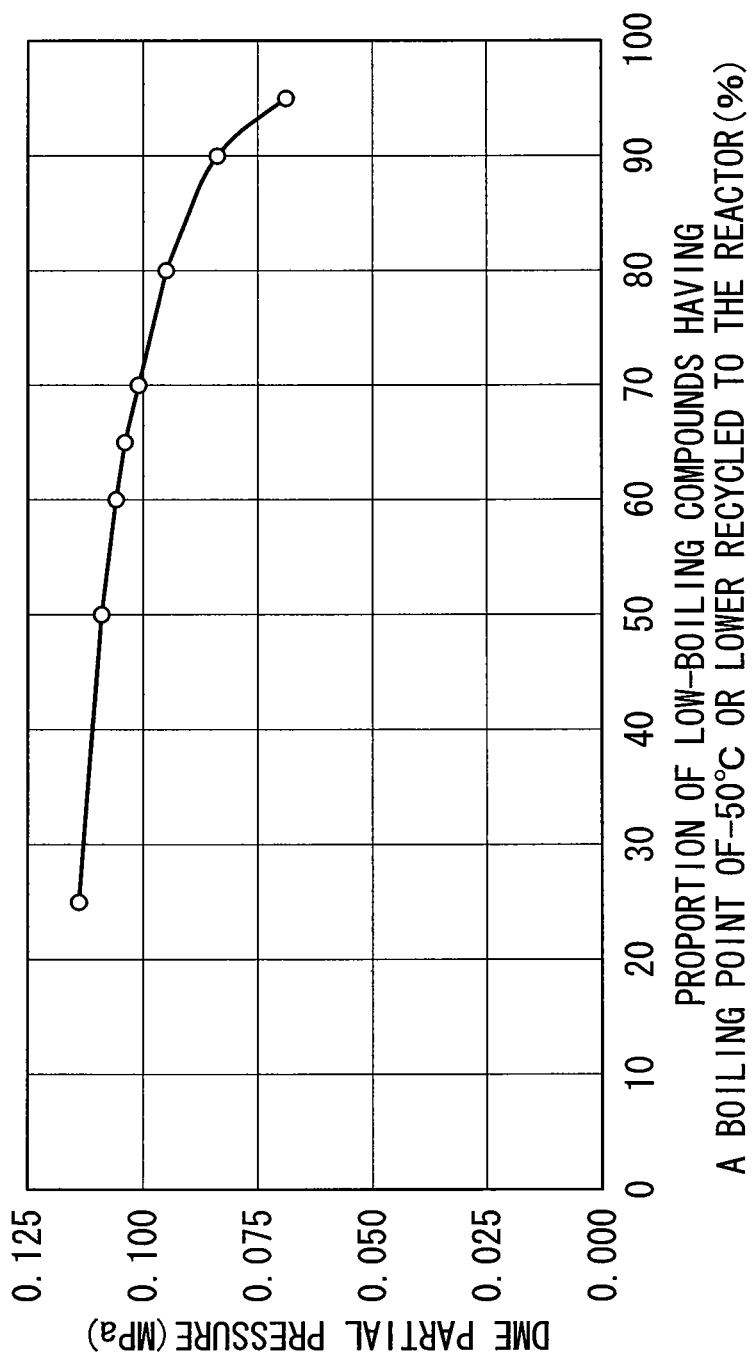
FIG. 2 is a graph to show a relationship of the proportion (%) of the low-boiling compounds having a boiling point of −50° C. or lower recycled to the reactor vs. the partial pressure (MPa) of dimethyl ether in the invention.

In addition, the partial pressure of dimethyl ether is plotted with respect to the proportion (%) of the low-boiling compounds having a boiling point of −50° C. or lower recycled to the reactor, which is shown in FIG. 2.

FIG. 2 shows that the partial pressure of dimethyl ether tends to decrease as the proportion of the low-boiling compounds having a boiling point of −50° C. or lower recycled to the reactor increases. As shown in FIG. 2, in the range of the recycled proportion of lower than 70%, the partial pressure of dimethyl ether slowly decreases as the proportion of the low-boiling compounds having a boiling point of −50° C. or lower recycled to the reactor increases; however, when the recycled proportion is over 70%, the partial pressure of dimethyl ether decreases, and when the recycled proportion is over 80%, the partial pressure of dimethyl ether decreases rapidly. That is, it was confirmed that when the proportion of the low-boiling compounds having a boiling point of −50° C. or lower recycled to the reactor is over 70%, the partial pressure of the raw material in the reactor can be effectively lowered so that the propylene yield is increased, and thereby propylene can be efficiently produced.

INDUSTRIAL APPLICABILITY

The invention can provide a process for producing propylene and an apparatus for producing propylene whereby propylene can be produced at a low cost using at least one of dimethyl ether and methanol and enhancing the propylene yield by inhibiting the catalyst deactivation, and thereby having very useful industrial applicability.

The invention claimed is:

1. A process for producing propylene, comprising the steps of:
    feeding at least one of dimethyl ether and methanol to a reactor to be reacted in the presence of a catalyst;
    supplying an obtained reaction product to a separator by which low-boiling compounds having a boiling point of −50° C. or lower at atmospheric pressure among the reaction product are separated;
    recycling at least 90% of a total amount of the separated low-boiling compounds to said reactor;
    converting at least a portion of the remainder of the separated low-boiling compounds to a $C_4$~$C_{10}$ hydrocarbon;
    recycling the $C_4$~$C_{10}$ hydrocarbon to said reactor; and
    maintaining a partial pressure of at least one of dimethyl and methanol in the reactor at 0.005 MPa-0.20 MPa.

2. The process according to claim 1, wherein at least a part of $C_4$~$C_6$ hydrocarbons separated by the separator are recycled to the reactor.

3. The process according to claim 1, wherein said catalyst is a MFI zeolite catalyst.

4. The process according to claim 1, wherein the catalyst is an alkaline earth metal-containing MFI zeolite catalyst, the MFI zeolite having a Si/Al molar ratio of from 10 to 300 and an alkaline earth metal/Al molar ratio of from 0.75 to 15.

5. The process according to claim 2, wherein the catalyst is an alkaline earth metal-containing MFI zeolite catalyst, the MFI zeolite having a Si/Al molar ratio of from 10 to 300 and an alkaline earth metal/Al molar ratio of from 0.75 to 15.

6. The process according to claim 3, wherein the catalyst is an alkaline earth metal-containing MFI zeolite catalyst, the MFI zeolite having a Si/Al molar ratio of from 10 to 300 and an alkaline earth metal/Al molar ratio of from 0.75 to 15.

* * * * *